United States Patent [19]

Joullié et al.

[11] 4,203,986
[45] May 20, 1980

[54] M-TRIFLUORO-METHYLPHENYL-PIPERAZINE

[75] Inventors: Maurice Joullié, Saint-Germain-en-Laye; Gabriel Maillard, Paris; Lucien Lakah, Paris; Christian J. M. Warolin, Paris; Yves R. A. Pascal, Paris, all of France

[73] Assignee: Metabio-Joullie, France

[21] Appl. No.: 869,277

[22] Filed: Jan. 13, 1978

[30] Foreign Application Priority Data

Jan. 14, 1977 [GB] United Kingdom ............... 1539/77

[51] Int. Cl.$^2$ ............... C07D 295/08; C07D 295/10; A61K 31/495
[52] U.S. Cl. ............................ 424/250; 544/357
[58] Field of Search ............... 544/394, 357, 392; 424/250

[56] References Cited

U.S. PATENT DOCUMENTS

| 3,170,926 | 2/1965 | Ash et al. | 544/395 |
| 3,253,989 | 5/1966 | Moser et al. | 544/395 |
| 3,637,705 | 1/1972 | Horrom et al. | 544/395 |
| 3,929,792 | 12/1975 | Bouchara | 544/394 |
| 3,953,449 | 4/1976 | Giudicelli et al. | 544/394 |

FOREIGN PATENT DOCUMENTS 2128713 10/1972 France.

Primary Examiner—Jose Tovar
Attorney, Agent, or Firm—Gordon W. Hueschen

[57] ABSTRACT

Compounds of the formula I

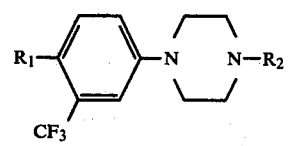

wherein $R_1$ represents a hydrogen or fluorine atom, and $R_2$ represents an alkyl group containing 2 to 6 carbon atoms, or a cycloalkyl or cycloalkyl-alkyl group containing 5 to 8 carbon atoms, each of these groups being substituted by one or two hydroxy groups or an oxo group and, if desired, also by a 4-(m-trifluoromethylphenyl)-piperazino or 4-(3-trifluoromethyl-4-fluorophenyl)-piperazino group with the proviso that, when $R_1$ represents a hydrogen atom, $R_2$ does not represent a monohydroxyalkyl group, and their pharmaceutically acceptable acid addition salts are novel and have therapeutic use, notably in the region of the central nervous system and in the cardiovascular region.

16 Claims, No Drawings

M-TRIFLUORO-METHYLPHENYL-PIPERAZINE

The present invention relates to derivatives of meta-trifluoromethylphenyl-piperazine and their therapeutical use, notably in the region of the central nervous system and in the cardiovascular region.

According to the present invention, there are provided compounds of the formula I

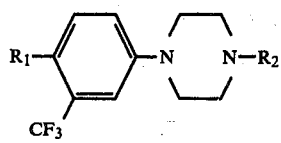

wherein
$R_1$ represents a hydrogen or fluorine atom, and
$R_2$ represents an alkyl group containing 2 to 6 carbon atoms or a cycloalkyl or cycloalkylalkyl group containing 5 to 8 carbon atoms, each of these groups being substituted by one or two hydroxy groups or an oxo group and, if desired, also by a 4-(m-trifluoromethylphenyl)-piperazino or 4-(3-trifluoromethyl-4-fluorophenyl)- piperazino group with the proviso that, when $R_1$ represents a hydrogen atom, $R_2$ does not represent a monohydroxyalkyl group,
and their pharmaceutically acceptable acid addition salts.

The invention comprises more particularly the compounds of the formula I wherein $R_1$ represents a hydrogen atom, and $R_2$ represents a 2,3-dihydroxypropyl, 2-hydroxycyclohexyl, 2-oxocyclohexylmethyl, 3-[4-(m-trifluoromethylphenyl)-piperazino]-2-hydroxypropyl, 2-oxo-cyclopentylmethyl, 2-hydroxy-cyclohexylmethyl, 3-[4-(m-trifluoromethylphenyl)-piperazino]-2-oxo-propyl, or 2-oxo-cycloheptylmethyl group, or $R_1$ represents a fluorine atom, and $R_2$ represents a 2-hydroxyethyl, 2-oxo-cyclohexylmethyl, 3-[4-(3-trifluoromethyl-4-fluoro-phenyl)-piperazino]-2-hydroxypropyl or 2,3-dihydroxypropyl group, as well as their pharmaceutically acceptable acid addition salts.

The compounds of the invention may be prepared by reaction of a compound corresponding to the formula II

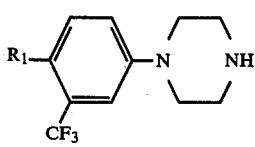

(wherein $R_1$ represents a hydrogen or fluorine atom) with a halogenated and/or epoxy derivative of radical $R_2$ defined above, or with a derivative $R_2H$ (wherein $R_2$ carries an oxo group) and formaldehyde. The reaction may be followed by an oxidation or reduction carried out in conventional manner. The acid addition salts may be obtained in conventional manner by reaction of the base of the formula I with a pharmaceutically acceptable acid.

Compounds of the formula II are known and available in commerce. N-m-Trifluoromethylphenylpiperazine ($R_1=H$) has been described in British Patent Specification No. 948,767 and N-(3-trifluoromethyl-4-fluorophenyl)-piperazine in U.S. Pat. No. 3,637,705.

The invention also provides pharmaceutical compositions comprising a compound of the formula I or a pharmaceutically acceptable acid addition salt thereof togther with a pharmaceutically acceptable carrier or diluent.

The invention further provides a method of treating a human patient which method comprises administering to the patient a compound of the formula I or a pharmaceutically acceptable acid addition salt thereof.

The following Examples illustrate the invention. In the Examples temperatures are given in degrees Centigrade.

EXAMPLE 1

3-[4-(m-Trifluoromethylphenyl)-piperazino]-propane-1,2-diol

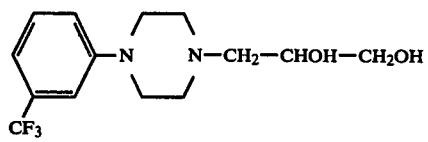

13.5 g (58.6 moles) m-Trifluoromethylphenyl-piperazine are dissolved in a mixture of 67.5 ml butanol and 7.5 ml 3-chloropropane-1,2-diol (90.5 mmoles). 10.6 g sodium carbonate in fine powder form are added and the mixture refluxed for sixteen hours with stirring. The solution is cooled and filtered and then the residue is rinsed with hot propanol and the solution evaporated. The residue is taken up in ether and a 10% sodium carbonate solution. The product is decanted, rinsed with water and evaporated. There is obtained an oil whose I.R., N.M.R. and mass spectra are consistent with the proposed structure.

The hydroiodide is prepared by adding concentrated hydroiodic acid to a 10% solution of the base in isopropanol. The product is filtered and recrystallised from isopropanol. 13.9 g (55% yield) of white crystals are obtained. Melting Point: 156–157° (LJ 1142).

$C_{14}H_{20}F_3I\ N_2O_2$ Calculated %: C 38.9; H 4.66; N 6.48; I 29.4; Found %: 38.6; 4.77; 6.40; 29.6.

EXAMPLE 2

2-[4-(m-Trifluoromethylphenyl)-piperazino]-cyclohexanol

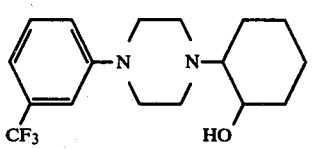

A mixture of 14 g (60 mmoles) m-trifluoromethylphenyl-piperazine and 5.88 g (6 ml, 60 mmoles) cyclohexane oxide are heated for 4 hours at 145°. The product is cooled and subjected to chromatography over 200 g silica. The elution is carried out successively with methylene chloride, and then chloroform, progressively enriched with methanol.

7.9 g (40% yield) of an oil separate, whose I.R., N.M.R. and mass spectra are consistent with the proposed structure. The base is placed in solution in acetone and, gradually, concentrated hydrochloric acid is added. The dihydrochloride is obtained. Melting Point: 225°–229° (LJ 1143).

$C_{17}H_{25}Cl_2F_3N_2O$. Calculated %: C 50.88; H 6.2; N 6.98; Cl 17.66; Found %: C 50.98; H 6.43; N 7.06; Cl 17.53.

EXAMPLE 3

2-[4-Trifluoromethylphenyl)-piperazino]-methyl-cyclohexanone

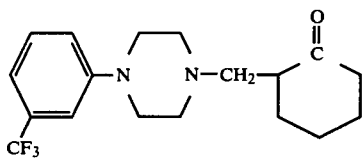

12.8 g (55.6 moles) m-Trifluoromethylphenyl-piperazine hydrobromide are introduced into 68 ml ethanol. There are added 2.0 g (66 mmoles) paraformaldehyde and 4.8 g (5.1 ml, 49 mmoles) cyclohexanone with stirring and then 0.025 ml hydrobromic acid concentrated to 48%. The mixture is then refluxed. The crystals dissolve gradually. The mixture is heated for eight hours and then left to cool. The crystals obtained are filtered and recrystallised from isopropanol to give 14.1 g (70% yield) of the hydrobromide. Melting Point: 175°–176° (LJ 1144).

$C_{18}H_{24}BrF_3N_2O$. Calculated %: C 51.22; H 6.19; N 6.65; Br 18.88; Found %: C 51.25; H 6.10; N 6.67; Br 18.97.

By neutralisation with 10% sodium carbonate in water, in the presence of benzene, there is obtained the free base in solution. This is dried and evaporated. The I.R., N.M.R. and mass spectra are consistent with the proposed structure.

Fumarate (LJ 1151) Melting Point: 145°

$C_{22}H_{27}F_3N_2O_5$. Calculated %: C 57.89; H 5.96; N 6.14; Found %: C 57.67; H 5.87; N 5.98.

EXAMPLE 4

1,3-bis[4-(m-Trifluoromethylphenyl)-piperazino]-propan-2-ol

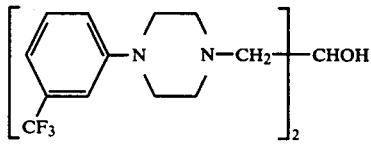

64 g m-Trifluoromethylphenyl-piperazine (0.28 mole) are placed in a flask heated by an oil bath. There are added, with stirring, 7.5 ml (0.096 mole) epichlorohydrin and the mixture is heated progressively over one hour to 120°. For the next 6 hours, the temperature is progressively raised by 10° per hour until the temperature of the oil bath attains 180°. The heating is continued at this temperature for another four hours and then the reaction mixture is left to cool. The reaction mixture is taken up in chloroform and N-sodium hydroxide, washed with water, dried and evaporated. The crude product is dissolved in ethanol and concentrated hydrochloric acid is added until an acid pH is reached. The hydrochloride is precipitated by addition of water. The product is filtered and recrystallised from a mixture of ⅓ ethanol to ⅔ water by volume. 46.5 g of the hydrochloride hemi-hydrate are obtained. Melting Point: 240°–245° (LJ 1145).

$C_{25}H_{32}Cl_2F_6N_4O$. ½ $H_2O$. Calculated %: C 49.43; H 5.63; N 9.22; Cl 11.67; Found %: C 49.70; H 5.81; N 9.24; Cl 11.64.

The hydrochloride is placed in suspension in chloroform and, gradually and with strong agitation, N-sodium hydroxide is added. When all is dissolved, the solution is washed with water saturated with sodium chloride, dried and evaporated. There is obtained an oil whose I.R., N.M.R. and mass spectra are consistent with the proposed structure. The fumarate hemi-hydrate is prepared in propanol. (LJ 1152).

$C_{33}H_{38}F_6N_4O_9$. ½ $H_2O$.

Calculated %: C 52.31; H 5.15; N 7.39; Found %: C 52.23; H 5.29; N 7.35.

The diphosphate is prepared in ethanol and recrystallised from ethanol. Melting Point : 190°–197° (LJ 1154).

$C_{25}H_{36}F_6N_4O_9P_2$.

Calculated %: C 42.14; H 5.09; N 7.86; P 8.69; Found %: C 42.02; H 5.21; N 7.99; P 9.10.

EXAMPLE 5

2-[4-m-Trifluoromethylphenyl)-piperazino]methyl-cyclopentanone

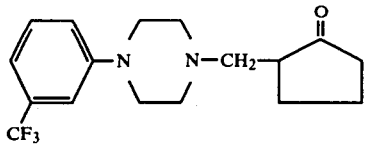

12.8 g (55.6 mmoles) m-Trifluoromethylphenyl-piperazine hydrobromide, 2.0 g (66 mmoles) paraformaldehyde and 4.10 g (49 mmoles) cyclopentanone are dissolved in 68 ml ethanol. There is added 0.025 ml hydrobromic acid concentrated to 48% and the mixture is heated under reflux for 16 hours. After cooling, the crystals, which are formed, are filtered and recrystallised from isopropanol. 12.9 g (65% yield) of the hydrobromide are obtained. Melting Point: 180°–185° (LJ 1160).

$C_{17}H_{22}Br F_3N_2O$. Calculated %: C 50.13; H 5.44; N 6.87; Found %: C 50.54; H 6.68; N 6.92.

The base, liberated with 0.1 N sodium hydroxide, is extracted with benzene. After drying and evaporation of solvent the I.R., N.M.R. and mass spectra are in accord with the proposed structure.

EXAMPLE 6

2-[4-(m-Trifluoromethylphenyl)-piperazino]-methyl-cyclohexanol

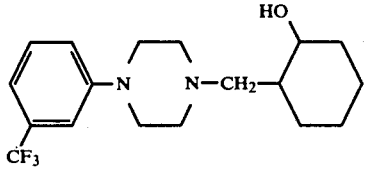

11.0 g (32 mmoles) 2-[4-(m-trifluoromethylphenyl)-piperazino] methyl-cyclophexanone obtained according to Example 3 are dissolved in ethanol and cooled. With stirring 10 g sodium borohyride are added gradually in small quantities. The progress of the reaction is followed on a thin layer of silica.

[The thin layer chromatography was carried out on a plate of fluorescent silica (Merck), eluting with chloroform containing 10% by volume methanol. The Dragendorff reagent is shown by pulverisation.]

When all is converted, there is added acetone and then water and finally N-sodium hydroxide. The mixture is extracted with ether, washed with water saturated with sodium chloride, dried over sodium sulphate and evaporated. There is obtained an oil from which there is prepared the fumarate in an isopropanol-water mixture.

9.3 g (63% yield) of the product are obtained.
Melting Point: 156°–158° (LJ 1161).

$C_{22}H_{29}F_3N_2O_5$ Calculated %: C 57.63; H 6.37; N 6.11; Found %: C 57.70; H 6.45; N 6.00.

By neutralisation of the fumarate, there is obtained the free base whose I.R., N.M.R. and mass spectra are in accord with the proposed structure.

EXAMPLE 7

1,3-bis[4-(m-Trifluoromethylphenyl-piperazino]-propan-2-one

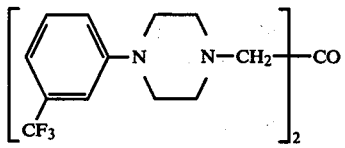

13.2 g (25.5 mmoles) 1,3-bis[4-(m-trifluoromethylphenyl)-piperazino]-propan-2-obtained according to Example 4 are dissolved in 132 ml anhydrous dimethylsulphoxide (DMSO), 15.76 g (76.5 mmoles) dicyclohexylcarbodiimide and then 56 mmoles anhydrous phosphoric acid are added and the mixture crystallised. The mixture is left for 48 hours at ambient temperature and then 1.8 ml water are added and the mixture stirred for 2 hours and filtered. The mixture is rinsed with ether, washed three times with saturated sodium bicarbonate solution. The product is dried, evaporated and subjected to chromatography over silica using as eluant methylene chloride and then chloroform enriched progressively with methanol. The I.R., N.M.R. and mass spectra of the base obtained are in accord with the proposed structure.

The hydrochloride hydrate is prepared in ether by addition of hydrochloric ether. 6.17 g (yield 40%) are obtained. Melting Point: 260°–265° (LJ 1163). $C_{25}H_{32}Cl_2F_6N_4O_2$. Calculated %: C 49.59; H 5.32; N 9.25; Cl 11.71; Found %: C 49.20; H 5.60; N 9.20; Cl 11.19.

EXAMPLE 8

2-[4-(m-Trifluoromethylphenyl)-piperazino]-methyl-cycloheptanone

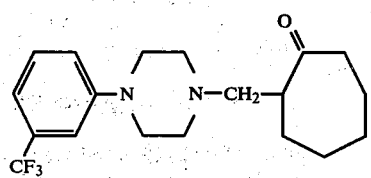

A mixture of 12.8 g (0.041 mole) m-trifluoromethyl-phenyl-piperazine hydrobromide, 5.47 g (0.04 mole) cycloheptanone, 2.0 g (0.066 mole) paraformaldehyde and 0.1 concentrated hydrobromic acid are heated under reflux for 12 hours in 68 ml ethanol. The mixture is left to cool, filtered and recrystallised from isopropanol.

9.47 g (53% Yield) of product (hydrobromide) are obtained. Melting Point=197.20 (LJ 1176)

$C_{19}H_{25}F_3N_2O$. HBr. Calculated %: C 52.42; H 6.02; N 6.43; Br 18.36; Base 8.14; Found %: C 52.36; H 6.16; N 6.35; Br 18.65; 80.6.

EXAMPLE 9

2-[4-(3-Trifluoromethyl-4-fluorophenyl)-piperazino]-ethanol

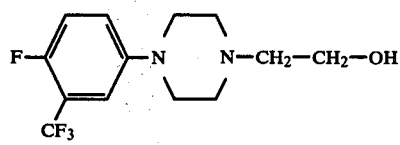

10 g (0.04 mole) 4-(3-Trifluoromethyl-4-fluorophenyl)piperazine and 7 g (0.056 mole) 2-bromoethanol are heated under reflux for 4 hours in 60 ml n-butanol. The mixture is left to cool, filtered and then recrystallised from ethanol.

9.15 g (61% yield) of white crystals (hydrobromide) are obtained. Melting Point (with decomposition)=248°–249°(LJ 1195).

$C_{13}H_{16}F_4N_2O$. HBr. Calculated %: C 41.84; H 4.59; N 7.51; Br 21.41; Base 78.3. Acid 21.7. Found %: C 41.69; H 4.58; N 7.42; Br 21.66; Base 79.7. Acid 22.1.

EXAMPLE 10

2-[4-(3-Trifluoromethyl-4-fluorophenyl)-piperazino]-methyl-cyclohexanone

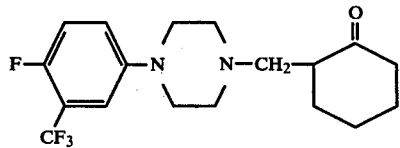

10.5 g (0.032 mole) 4-(3-Trifluoromethyl-4-fluorophenyl)-piperazine, 5 ml (4.78 g, 0.048 mole) cyclohexanone, 1.6 g (0.053 mole) paraformaldehyde and 0.05 ml concentrated hydrochloric acid are heated for 14 hours under reflux in 53 ml ethanol. After cooling, the solvent is evaporated and the residue recrystallised from isopropanol.

4.6 g (33% Yield) of product (hydrobromide) are obtained. Melting Point =190° (LJ 1196).

$C_{18}H_{21}F_4N_2C$. HBr. Calculated %: C 49.33; H 5.06; N 6.39; Found %: C 49.21; H 5.22; N 6.37.

EXAMPLE 11

1,3-bis[4-(3-Trifluoromethyl-4-fluorophenyl)-piperazino)-propan-2-ol

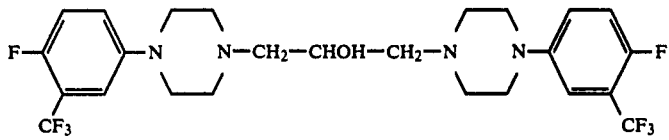

A mixture of 10 g (0.04 mole) 4-(3-trifluoromethyl-4-fluorophenyl)-piperazine and 1.56 ml (1.84 g, 0.02 mole) epichlorohydrin are stirred for 2 hours at ambient temperature. 2.8 g (0.02 mole) potassium carbonate are added and the mixture heated under reflux for 2¼ hours. The mixture is filtered, washed with propanol, and the organic solution evaporated. The residue is then extracted with ether and washed with 0.1 N-sodium hydroxide solution, and then with saturated sodium chloride solution. The etherified solution is dried over sodium sulphate. The crude base is obtained by evaporation and then dissolved in ethanol at 90° C. and 2 equivalents of crystallised phosphoric acid added. The crystals are filtered after cooling in a refrigerator and recrystallised from ethanol at 90°.

4.28 g (28% Yield) of white crystals are obtained. Melting Point = 190°(diphosphate). (LJ 1198).

$C_{25}H_{38}F_8N_4O \cdot 2H_3PO_4 \cdot H_2O$. Calculated %: C 39.17; H 4.73; N 7.30; Found %: C 38.98; H 4.65; N 7.25.

EXAMPLE 12

3-[4-(3-Trifluoromethyl-4-fluorophenyl)-piperazino]-propane-1,2-diol

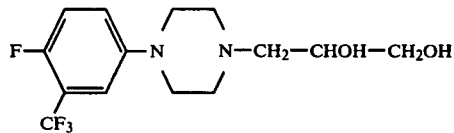

A mixture of 4.5 g (0.018 mole) 4-(3-trifluoromethyl-4-fluorophenyl)-piperazine and 4.0 g (0.026 mole) bromopropane-1,2-diol are heated under reflux. 2.8 g (0.02 mole) potassium carbonate are added gradually during the course of the reaction.

After 11 hours of heating, the mixture is left to cool, the butanol evaporated and the residue taken up in water and extracted with chloroform. 6.7 g Of a red oil which crystallises are obtained. This oil is subjected to chromatography over silica eluting with chloroform containing 2% methanol.

The separation is followed on thin layers. The fractions containing the product are combined and evaporated. 4.5 g Of a yellow oil are obtained. This oil is dissolved in boiling isopropanol where 1 ml concentrated hydrobromic acid is added gradually to it. By cooling, there are obtained crystals which are filtered.

Obtained: 3,45 g (47% yield) of white crystals (hydrobromide). Melting Point = 222° (LJ 1211).

$C_{14}H_{18}F_4N_2O_2 \cdot HBr$. Calculated %: C 41.70; H 4.75; N 6.95; Found %: C 41.76; H 4.78; N 6.93.

The compounds of the invention have been subjected to pharmacological study.

Acute toxicity in Mice

The compounds are administered in increasing doses (in arithmetic progression) to groups of five ♀ SWISS, EOPS, NMRI/Han mice of the EVIC CEBA strain and having a mean weight of 22 g.

For intravenous administration the compounds are dissolved in distilled water, for oral administration they are suspended in 10% gum arabic solution (volume administered: 0.5 ml/22 g body weight).

The LD 50's are calculated according to the method of KARBER and BEHRENS (B.) (Arch. Exp. Path. Pharmakol. 1935, 177, 379–388).

For each administration method, there is indicated:
LD 0 or maximum dose tolerated.
LD 100 or minimum lethal dose.

The number of animals surviving in the different groups is definitively verified 15 days after administrating the compounds.

The results are summarised in Table 1 below:

TABLE 1

| Compounds | Doses in mg/kg | | | | | |
|---|---|---|---|---|---|---|
| | Intravenous Administration | | | Oral Administration | | |
| | LD 0 | LD 50 | LD 100 | LD 0 | LD 50 | LD 100 |
| LJ 1142 | 225 | 252 | 300 | 750 | 1125 | 1500 |
| LJ 1143 | 56 | 69 | 81 | 250 | 625 | 1000 |
| LJ 1144 | 37.5 | 61 | 75 | 1250 | 1825 | 2250 |
| LJ 1145* | — | — | — | 200 | 580 | 1000 |
| LJ 1152* | 25 | 36 | 50 | 125 | 225 | 375 |
| LJ 1154* | 25 | 37.5 | 44 | 50 | 135 | 200 |
| LJ 1160 | 62,5 | 74 | 87.5 | 500 | 975 | 1500 |
| LJ 1161 | 50 | 66 | 87.5 | 750 | 1500 | 2000 |
| LJ 1163 | 12.5 | 18 | 22.5 | 125 | 180 | 250 |
| LJ 1176 | — | — | — | 1500 | 1950 | 2500 |
| LJ 1195 | — | — | — | 300 | 844 | 1250 |
| LJ 1196 | — | — | — | 625 | 937 | 1250 |
| LJ 1198 | — | — | — | 50 | 225 | 400 |
| LJ 1121 | — | — | — | 500 | 925 | 1250 |

*These three compounds correspond to different salts of the same base:
LJ 1145 dihydrochloride
LJ 1152 difumarate
LJ 1154 diphosphate

PHARMACOLOGICAL STUDY

I—Action in the region of the central nervous system

A—Experimental methods (1) Action on the spontaneous motor activity in mice 30 minutes after administration per os of the test compounds, the mice (12 per group) are installed in individual cages of a BOISSIER activity measuring cupboard (BOISSIER (J.R.), SIMON (P), Arch. Int. Pharmacodyn, 1965, 158, 212–221) and move about before two photoelectric cells placed according to the rectangular co-ordinates. Meters register the movements over 20 minutes. The results are expressed as percentages of variation of the motor activity compared with the control group of animals.

(2) Action on the body temperature of the mouse

The rectal temperature of mice (groups of 10 animals) is measured with the aid of an ELLAB thermocouple.

The test compounds are then administered orally and the temperature taken 30 minutes, 1 hour, 2 hours, 3 hours, 4 hours, 5 hours and 6 hours later.

(3) Action on the narcotic effect of pentobarbital in the mouse 30 minutes after administration of the compounds, the mice (groups of 10 animals) receive an injection of pentobarbital at a dose (50 mg/kg i.v.) which, in control animals which have only received administration vehicle (10% gum arabic solution), induces a sleep of about 30 to 60 minutes. The hypnosis time of each mouse is counted in minutes from the moment when the animal may be placed without resistance on its back until that when it spontaneously gets back on its feet.

In the treated groups and the control group, the mean sleep time is calculated and the results are expressed as percentages of variation based on the control group.

(4) Action on the traction test in mice (groups of 10 animals)

This test described by COURVOISIER (S.) (J. Clinic. Exp. Psychopath., 1956, 17, 25) determines the presence or absence of re-establishment in a mouse placed by its front feet on a horizontal metal film. 30 minutes, 1 hour and 2 hours after administration p.o. of the test compounds, the percentage of mice, which are unable to touch the film with one of their back feet in less than 5 seconds, is noted.

(5) Test of the anti-convulsant action against electric shock in mice. (groups of 10 animals)

30 minutes after administration of the test compounds, the protection induced against tonic crisis (extension of back feet) provoked by supramaximal transcranial electric stimulation (13 to 16 mA for 0.1 second) is tested.

The results are expressed as percentages of the protection compared with a control group.

(6) Action on the toxicity of Amphetamine compounds in the mice. (groups of 10 animals)

30 minutes after administration of the test compounds, amphetamine bitartrate is injected interperitioeally at a dose of 10 mg/kg (dose giving substantially 100% mortality) to mice in groups of 10 in boxes 12×18×13 cm. The number of animals surviving 24 hours after the amphetamine administration is noted.

(7) Test on the cataleptic action in rats (groups of 5 animals)

After administration p.o. of the test compounds, the degree of catalepsy is noted every 30 minutes for 6 hours by the test of crossing of the homolateral feet according to BOISSIER (J.R.) and SIMON (P.) (Therapy, 1963, 18, 1257-1277) and using the following notation:

0 = animal which is not cataleptic
132 animal conserving position on one side only
2 = animal conserving position on both sides The results are shown in Table 2 below.

TABLE 2

| Compounds | Dose in mg/kg per os | Spontaneous motor activity (% of variation) | Pentobarbitol hypnosis time (% of variation) | Body temperature (Variation in °C.) | Traction test (% of animals which fal) | Effect against Electric shock (% of protection) | Effect on the toxicity of amphetamine compounds (% of protection) |
|---|---|---|---|---|---|---|---|
| LJ 1142 | 112 | −55% | +92% | −1°7 | 100% | 100% | 10% |
| LJ 1144 | 182 | −88% | +212% | −3°2 | 90% | 100% | 65% |
| LJ 1145 | 58 | −56% | +74% | −2°1 | 60% | 87% | 0 |
| LJ 1160 | 100 | −28% | +207% | −0°5 | 80% | 90% | 90% |
| LJ 1161 | 150 | −68% | +137% | −0°6 | 70% | 90% | 80% |
| LJ 1176 | 200 | −66% | +147% | −1°1 | 40% | 70% | 50% |
| LJ 1195 | 85 | −27% | +319% | 0 | 80% | 80% | 0 |
| LJ 1196 | 95 | −61% | +300% | −0°9 | 100% | 90% | 10% |
| LJ 1211 | 100 | −44% | +184% | −1° | 90% | 10% | 0 |

B—Results (Table 2)

The different compounds studied reduce motor activity and body temperature, agility and motor co-ordination; they increase the narcosis of pentobarbital and oppose the convulsant effects of electric shock.

The results are the reflection of a sedative, tranquillising and anxiety relieving effect.

Although LJ 1144, 1160, 1161 and 1176 reduce the toxicity of amphetamine compounds, the absence of cataleptic effect does not permit the conclusion of a neuroleptic effect for the four compounds.

II—Antitussive action (1) In the guinea pig

The technique used is that of SIECKMANN (W.) (in "Notions techniques de Pharmacologie generale" by Michel COLOT, page 75, Masson, Edit, 1972).

The guinea pigs ♀ of mean weight 400 g, unanaesthesised, are subjected to the tussigenic effect of aerosols of a 7.5% aqueous citric acid solution. The animals are placed one by one in a cylindrical chamber having at its two extremities two canals, one serving as entrance for the aerosol and the other as its exit.

On the exit tube there is a lateral connection to a MERCURY gas pressure differential gauge joined to an RACIA counter. An adjustable screw clamp placed on the exit tube downstream of the lateral canal permits regulation of the sensitivity of the system such that the normal respiration of the animal only registers very weakly and that displacement of air in the chamber provoked by coughing attack is recorded clearly in the form of vertical traces.

Each guinea pig is first submitted to a control test for 5 minutes. One hour later it receives the test compound. It is replaced in the chamber for 5 minutes, 1 hour after oral administration of the compound.

The number of coughing attacks before and after administration is counted and the percentage inhibition is calculated.

Table 3 shows that the test compounds possess valuable antitussive activity. LJ 1144, 1152, 1154, 1161, 1163 and 1176 are also active if not more active than codeine.

TABLE 3

| Number of Animals | Compounds | Doses in mg/kg p.o. | Percentages of inhibition of coughing |
|---|---|---|---|
| 25 | Controls | — | 15% |
| 10 | Codeine | 35 | 64% |
| 26 | Codeine | 70 | 71% |
| 10 | LJ 1144 | 182 | 75% |
| 15 | LJ 1145 | 58 | 58% |
| 5 | LJ 1152 | 22 | 64% |
| 5 | LJ 1152 | 72 | 75% |
| 5 | LJ 1154 | 6.75 | 66% |
| 10 | LJ 1154 | 13.5 | 78% |
| 6 | LJ 1160 | 100 | 50% |
| 6 | LJ 1161 | 150 | 75% |
| 10 | LJ 1163 | 9 | 64% |
| 11 | LJ 1163 | 18 | 78% |
| 5 | LJ 1176 | 200 | 78% |
| 5 | LJ 1198 | 22 | 50% |

(2) In the cat

The classical technique of Domenjoz (R.) (Arch. Exper. Path. Pharmakol. 1952, 215, 19–24,), which comprises obtaining coughing by stimulation of the superior larynx nerve, was used.

The cats all thriving, male or female of weight between 1.5 and 2.5 kg (test on 10 cats) are anaesthesised by nembutal at a dose of 30 mg/kg interperitoneally.

A cannula having three branches is placed in the trachea. Two of the branches are connected to a device for registering intratracheal pressure (MERCURY gas pressure gauge connected to an RACIA polygraph) The third branch allows elimination of part of the respiratory volume.

A cannula is placed in the femoral vein for administration of the test substances.

The superior larynx nerve is isolated and the stimulation electrode (RACIA stimulator) is placed on the intact (unbound) nerve. The stimulation parameters are as follows: frequency: 5 cycles per sec, amplitude: 5 millisec, voltage: 4 to 6 volts, duration: 15 to 45 sec. (according to the sensitivity of the animal).

There are carried a minimum of 3 stimulations spaced by 5 minutes and provoking coughing attacks of the same severity. The compound is then administered intravenously. The stimulation is then carried out every 5 minutes. If the compound reduces or suppresses the coughing the stimulation is continued until the reappearance of coughing to approximately the same degree as the initial coughing.

The results are expressed as a percentage reduction in the number of coughs. They are summarized in Table 4 and show that 4 compounds selected from the preceding test are equally active on coughing in cats, the effects of LJ 1152 and 1154 are comparable with those of codeine.

TABLE 4

| Compounds | Doses i.v. | % maximum reduction in the number of coughs | Delay in the disappearance of protective effect |
|---|---|---|---|
| LJ 1144 | 12 mg/kg | 85 | 45 min–60 min |
| LJ 1152 | 3.6 mg/kg | 76 | 30 min–45 min |
|  | 7.2 mg/kg | 100 | 60 min–90 min |
| LJ 1154 | 4 mg/kg | 80 | 30 min–60 min |
|  | 8 mg/kg | 100 | 75 min–90 min |
| LJ 1163 | 1.8 mg/kg | 50 | Fleeting |
|  | 3.6 mg/kg | 62 | 15 min–30 min |
| Codeine | 3.5 mg/kg | 100 | 30 min–60 min |

III—Conclusion of pharmacological study

The derivatives of the present invention are endowed with sedative and tranquillising and antitussive properties.

The therapeutical indications resulting from the pharmacological studies concern:

anxiety, hyperemotivity, neurotic states, character troubles, functional troubles, neuro-vegatitive dystonis, coughing irritation, spasmodic coughing, productive and unproductive coughing, tracheal coughing, rhinopharyngitis, acute or chronic broncho-pneumopathy, allergic coughing, reactional coughing of pleural or neoplasic origin. This antitussive action is all the more interesting as it is not accompanied by depressive respiratory effect and as it respects expectoration.

Compounds of the invention may be administered orally, rectally and parenterally.

For all administration the mean posology is a function of the therapeutic indication and the nature of the compound concerned. An indicative standard of posology for an adult may comprise between 0.5 and 10 mg/kg orally and 0.5 to 5 mg parenterally.

The preferred pharmaceutical forms are tablets, capsules, drinkable suspensions, suppositories, aerosols, injectable solutions, etc.

We claim:

1. A compound of the formula

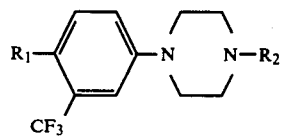

wherein $R_1$ is selected from a hydrogen or fluorine atom, and $R_2$ is selected from the group consisting of an alkyl group containing 2 to 6 carbon atoms and which is substituted by at most two hydroxy groups or an oxo group and also by a 4-(m-trifluoromethylphenyl)-piperazino or 4-(3-trifluoromethyl-4-fluoro-phenyl)-piperazino group, and pharmaceutically-acceptable acid addition salts thereof.

2. A compound according to claim 1 wherein $R_1$ represents a hydrogen atom, and $R_2$ is selected from the group consisting of:

a 3-[4-(m-trifluoromethylphenyl)-piperazino]-2-hydroxypropyl and a 3-[4-(m-trifluoromethylphenyl)-piperazino]-2-oxo-propyl group;

and pharmaceutically-acceptable acid addition salts thereof.

3. A compound according to claim 1 wherein $R_1$ represents a fluorine atom, and $R_2$ is 3-[4-(3-trifluoromethyl-4-fluorophenyl)-piperazino]-2-hydroxypropyl, and pharmaceutically-acceptable acid addition salts thereof.

4. A compound according to claim 1 which is selected from 1,3-bis[4-(m-trifluoromethylphenyl)-piperazino]-propan-2-ol, and its hydrochloride, fumarate and diphosphate.

5. A pharmaceutical composition which contains a compound of the formula

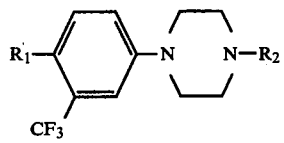

wherein
- R₁ is selected from a hydrogen or fluorine atom, and
- R₂ is selected from the group consisting of an alkyl group containing 2 to 6 carbon atoms which is substituted by one or two hydroxy groups or an oxo group and also by a 4-(m-trifluoromethylphenyl)-piperazino or 4-(3-trifluoromethyl-4-fluoro-phenyl)-piperazino group, or a pharmaceutically-acceptable acid addition salt thereof, together with a pharmaceutically-acceptable carrier or diluent.

6. A pharmaceutical composition according to claim 5 wherein
- R₁ represents a hydrogen atom, and
- R₂ is selected from the group, consisting of 3-[4-(m-trifluoromethylphenyl)-piperazino]-2-hydroxypropyl and 3-[4-(m-trifluoromethylphenyl)-piperazino]-2-oxo-propyl.

7. A pharmaceutical composition according to claim 5 wherein
- R₁ represents a fluorine atom, and
- R₂ is 3-[4-(3-trifluoromethyl-4-fluorophenyl)-piperazino]-2-hydroxypropyl or a pharmaceutically-acceptable acid addition salt thereof.

8. A pharmaceutical composition according to claim 5 which contains a compound selected from 1,3-bis[4-(m-trifluoromethylphenyl)-piperazino]-propan-2-ol, and its hydrochloride, fumarate and diphosphate.

9. A method of treating a human patient which comprises administering to the patient a therapeutically effective amount of a compound of the formula

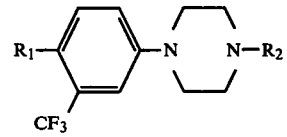

wherein
- R₁ is selected from a hydrogen or fluorine atom, and
- R₂ is selected from the group consisting of an alkyl group containing 2 to 6 carbon atoms which is substituted by one or two hydroxy groups or an oxo group and also by a 4-(m-trifluoromethylphenyl)-piperazino or 4-(3-trifluoromethyl-4-fluoro-phenyl)-piperazino group, or a pharmaceutically-acceptable salt thereof.

10. A method according to claim 9 wherein there is administered a compound selected from 1,3-bis[4-(m-trifluoromethylphenyl)-piperazino]-propan-2-ol, and its hydrochloride, fumarate and diphosphate.

11. A compound of the formula

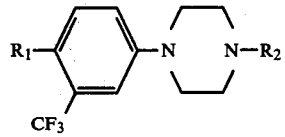

wherein
- R₁ is selected from the group consisting of hydrogen and fluorine, and R₂ is selected from the group consisting of
  - 3-[4-(m-trifluoromethylphenyl)-piperazino]-2-hydroxypropyl,
  - 3-[4-(m-trifluoromethyl-4-fluorophenyl)piperazino]-2-hydroxypropyl, and
  - 3-[4-(m-trifluoromethylphenyl)piperazino]-2-oxo-propyl, and pharmaceutically-acceptable acid addition salts thereof.

12. A compound according to claim 11, wherein R₁ is hydrogen and R₂ is 3-[4-(m-trifluoromethylphenyl)-piperazino]-2-hydroxypropyl, and the pharmaceutically acceptable acid addition salts thereof.

13. A compound according to claim 11, wherein R₁ is fluorine and R₂ is 3-[4-(m-trifluoromethyl-4-fluorophenyl)piperazino]-2-hydroxypropyl, and the pharmaceutically acceptable salts thereof.

14. A compound according to claim 11, wherein R₁ is hydrogen and R₂ is 3-[4-(m-trifluoromethylphenyl)-piperazino]-2-oxopropyl, and the pharmaceutically acceptable salts thereof.

15. A pharmaceutical composition comprising a compound according to claim 11, together with a pharmaceutically acceptable diluent.

16. A method of treating a human patient in need of central nervous system treatment, i.e., sedation, tranquilization or antitussive treatment, which comprises administering to such patient an effective amount of a compound of claim 11 to accomplish such treatment.

* * * * *

UNITED STATES PATENT AND TRADEMARK OFFICE
CERTIFICATE OF CORRECTION

PATENT NO. : 4,203,986
DATED : May 20, 1980
INVENTOR(S) : Maurice Joullie', Gabriel Maillard, Lucien Lakah, Christian J. M. Warolin and Yves R. A. Pascal It is certified that error appears in the above—identified patent and that said Letters Patent is hereby corrected as shown below:

Col. 2, line 6; "togther" should read -- together --
Col. 2, lines 13 & 14; "Centrigrade" should read -- Centigrade --
Col. 2, line 27; "(58.6 moles)" should read -- (58.6 mmoles) --
Col. 3, line 19; "(55.6 moles)" should read -- (55.6 mmoles) --
Col. 4, line 46; "6.68" should read -- 5.68 --
Col. 4, line 66; "cyclophexanone" should read -- cyclohexanone --
Col. 4, line 68; "borohyride" should read -- borohydride --
Col. 5, line 34; "2-obtained" should read -- 2-ol obtained --
Col. 6, line 5; "0.1 concentrated" should read -- 0.1 ml concentrated --
Col. 6, line 11; "197.20 (LJ" should read -- 197° (LJ --
Col. 6, line 13; "Base 8.14" should read -- Base 81.4 --
Col. 6, lines 36 & 37; "24- 8°" should read -- 248° -- this number should not be hyphenated.
Col. 8, line 39 in Table 1, Col. 2, line 7; "62,5" should read -- 62.5 --
Col. 10, line 2; "132 animal" should read -- 1 = animal --
Col. 10, Table 2, Col. 2, the heading "Dose in mg/kg per os" should read -- Doses in mg/kg per os --
Col. 10, Table 2, Col. 6, in the heading, last line; "which fal)" should read -- which fall) --
Col. 13, line 23; "group," delete the comma after the word "group"

Signed and Sealed this

Twenty-first Day of October 1980

[SEAL]

Attest:

SIDNEY A. DIAMOND

Attesting Officer

Commissioner of Patents and Trademarks